United States Patent [19]

El-Rashidy

[11] Patent Number: 5,256,652

[45] Date of Patent: Oct. 26, 1993

[54] TOPICAL COMPOSITIONS AND METHODS FOR TREATMENT OF MALE IMPOTENCE

[75] Inventor: Ragab El-Rashidy, Deerfield, Ill.

[73] Assignee: Pharmedic Co., Wheeling, Ill.

[21] Appl. No.: 573,518

[22] Filed: Aug. 27, 1990

Related U.S. Application Data

[63] Continuation-in-part of Ser. No. 119,799, Nov. 12, 1987, abandoned.

[51] Int. Cl.⁵ .................. A61K 31/47; A61K 31/715
[52] U.S. Cl. ...................... 514/58; 514/307; 514/385
[58] Field of Search ............ 514/307, 385, 58

[56] References Cited

U.S. PATENT DOCUMENTS

| | | | |
|---|---|---|---|
| 4,018,927 | 4/1977 | Voorhees | 514/307 |
| 4,311,707 | 1/1982 | Birnbaum et al. | 514/573 X |
| 4,801,587 | 1/1989 | Voss et al. | 514/248 |

FOREIGN PATENT DOCUMENTS

WO85/02767 7/1985 World Int. Prop. O. .

OTHER PUBLICATIONS

Chemical Abstracts 103:11280n (1985).

*Primary Examiner*—Leonard Schenkman
*Attorney, Agent, or Firm*—Dressler, Goldsmith, Shore, Sutker & Milnamow, Ltd.

[57] ABSTRACT

A topical composition which enhances the maintenance of penis erection is disclosed. An effective dosage of a peripheral vasodilator, an absorption enhancer and, optionally, a vasoconstrictor and an alpha receptor blocker are combined with a pharmacologically acceptable topical vehicle to produce the composition.

21 Claims, 1 Drawing Sheet

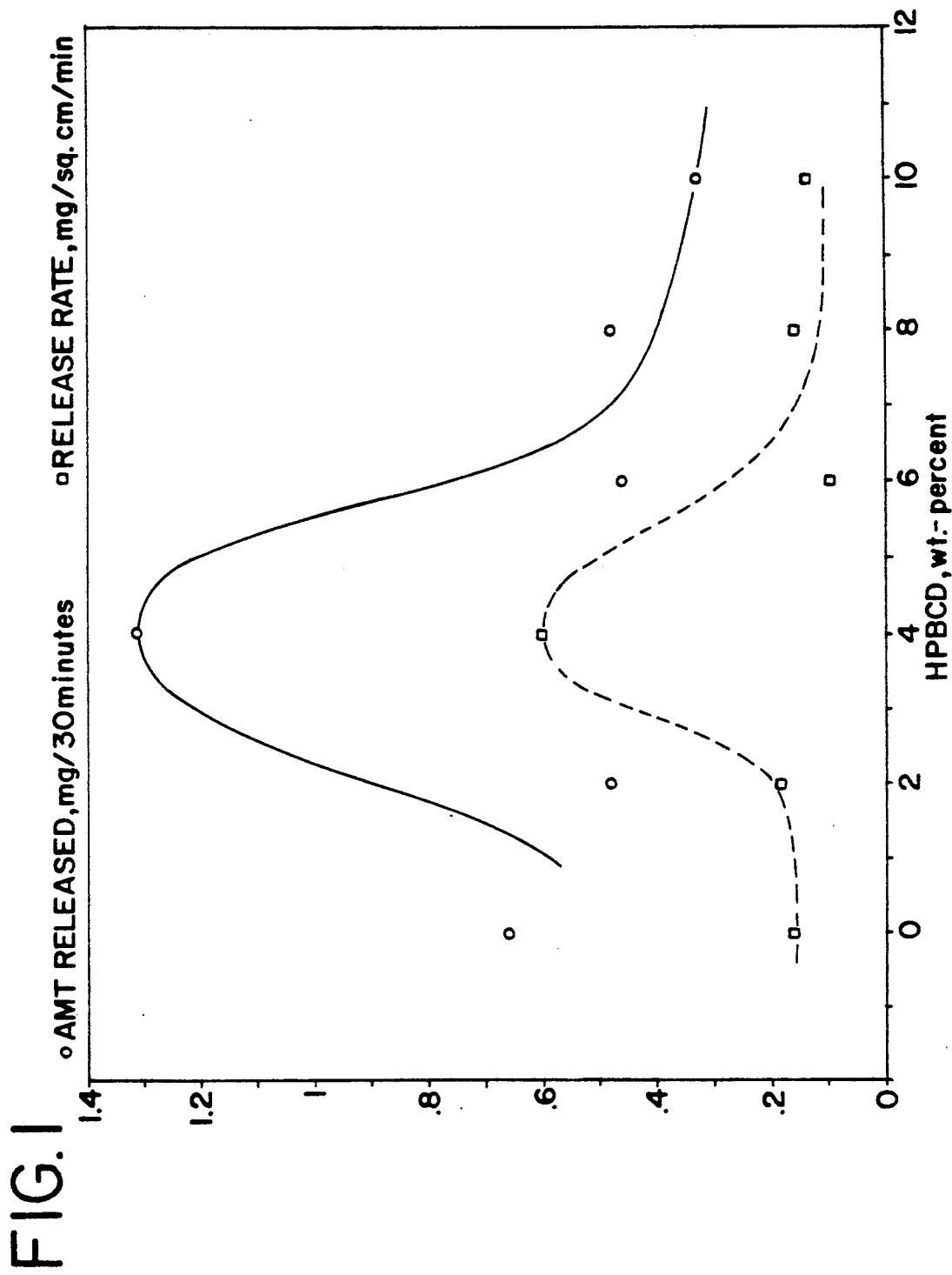

TOPICAL COMPOSITIONS AND METHODS FOR TREATMENT OF MALE IMPOTENCE

CROSS REFERENCE TO RELATED APPLICATION

This is a continuation-in-part application of copending U.S. Ser. No. 119,799, filed Nov. 12, 1987, now abandoned.

TECHNICAL FIELD

This invention relates to a composition to treat male impotence and in particular a topically administered composition.

BACKGROUND OF THE INVENTION

Impotence may be defined as the inability to develop or sustain an erection sufficient to conclude coitus. Many men are afflicted with a degree of impotence. There are psychological and physiological reasons for this inability.

The physiology of an erection involves nerve impulses which signal certain muscles to relax. These muscles, which are usually contracted, restrict arteries in the penis. When relaxed, the muscles permit a significant increase in blood flow. Three groups of erectile tissue within the penis become engorged with blood and, in turn, less flaccid. The filled tissue and the muscle structure of the penis depress adjacent veins. The flow of blood out of the penis is thus restricted which contributes to the erection. Damage to these nerves and blood vessels is a physiological reason for impotency.

Diabetes causes damage to both nerves and blood vessels. Thus diabetes often causes impotency. A significant percent of all diabetic men will suffer from impotency.

The most widely used solution for impotency involves implants which are, in essence, internal prostheses. There are two basic types of such prostheses. One type utilizes internal semi-rigid rods which can be bent up or down. The second type involves a surgically implanted pump which transfers fluid from an implanted fluid reservoir to an inflatable device in the penis.

These methods of correcting impotency have major shortcomings. The semi-rigid type does not allow the patient to control rigidity. The pump type requires hours of surgery on the penis, scrotum and abdomen and requires several days of hospitalization. Both types require surgery and are expensive. Also, once a prosthesis is implanted it makes a natural erection all but impossible.

External devices also have been used to produce and enhance an erection. Typically these devices are tourniquet-like and fit tightly around the shaft of the penis. The flow of blood from the penis through the surface veins is thereby restricted. However, because the deep dorsal vein is generally not effectively depressed, blood exiting the penis is not satisfactorily restricted. Thus the device's duration of effectiveness is relatively short. These external devices exhibit various other shortcomings including discomfort to both the user and sex partner and lack of efficacy in that the user might not achieve the desired usefulness as frequently as desired and to the extent preferred.

Drugs also can be used to induce an erection. Illustrative of this is U.S. Pat. No. 4,127,118 to Latorre which teaches the use, by injection, of a sympathomimetic amine or an adrenergic blocking agent. Latorre further states that other agents within the histamine and epinephrine groups may also be used when considered appropriate; however, while histamine is a vasodilator, epinephrine is a known vasoconstrictor. Both the chemical structure of the contemplated drugs as well as the contemplated mode of delivery distinguish the present invention from that of Latorre.

A shortcoming of Latorre is the method of delivery of the drugs. In this invasive approach, two needles are used to inject two of the three groups of erectile tissue with the drug. Thus only two of the three groups of erectile tissue respond to the treatment. This is obviously less desirable than having all three groups of erectile tissue engorged.

Being invasive, Latorre has other shortcomings. Injections are usually painful. These injections must be done in a well-lit area which is not always possible or desirable. There are health risks including hematoma, infection and scarring. If self-injection is resorted to, the drug administration is likely to be by a non-medically qualified person. As a dual needle syringe is required, there are two undesirable opportunities to hit a vein which would then dilate and allow excessive blood flow out of the penis. With two syringes there is also a greater likelihood of hitting a nerve. While Latorre teaches that his treatment can sustain an erection for 2 or 3 hours, this may be embarrassing in certain situations. In contradistinction, the present invention, because of its ease of use, overcomes the shortcomings of Latorre. All three groups of erectile tissue are engorged. There are no needles with their aforementioned shortcomings. The result is greater patient compliance. This greater compliance naturally results in the composition having a greater therapeutic value.

Birnbaum et al. U.S. Pat. No. 4,311,707 teaches the topical administration of prostaglandins or synthetic analogues of the PGE, PGA and PGF$\beta$ prostaglandin types to improve peripheral circulation. One alleged use is to treat impotency.

A comparison of chemical structures again differentiates the prostaglandin therapy of Birnbaum et al. and the peripheral vasodilators therapy contemplated by the present invention.

Voss et al. U.S. Pat. No. 4,801,587 describes the topical or intra-urethral administration of a vasodilator or alpha-blocker to relieve impotence by improving localized circulation. The vasodilator or alpha-blocker is combined with one or more carriers and an ointment base when administered topically. Papaverine is the vasodilator preferred in Voss et al. Dimethyl sulfoxide (DMSO) is stated to be the preferred carrier in the topically administered formulation; however, this carrier has not been approved for use by the U.S. Food and Drug Administration. Moreover, DMSO also has the undesirable effect of enhancing the systemic absorption of the vasodilator.

The problem with topically administered drugs is their limited penetration of the drug through the skin. Skin is a natural barrier and resists penetration of topically administered drugs. Without the presence of an enhancer in the topical drug compositions of Birnbaum et al. and Voss et al., only a small portion of the drug in the composition actually penetrates the skin.

The present invention provides a male impotence treatment which avoids the shortcomings of the prior art and enhances the maintenance of penis erection.

SUMMARY OF THE INVENTION

The present invention contemplates a topical composition and method that enhance the maintenance of penis erection. This composition comprises a peripheral vasodilator, a pharmacologically acceptable enhancer to facilitate absorption of the vasodilator and a pharmacologically acceptable topical vehicle for the vasodilator.

The peripheral vasodilator and the hydroxypropyl-β-cyclodextrin are present in a molar ratio in the range of about 1:0.8 to about 1:1.4 respectively, preferably, about 1:1. Papaverine is particularly preferred as the peripheral vasodilator.

Maintenance of penis erection may be further enhanced by restricting blood flow from the penis after the erection is enhanced by the peripheral vasodilator. This may be accomplished either by the addition of a slow acting vasoconstrictor to the composition or by utilizing a mechanical device such as an external, tourniquet-like device which is placed around the shaft of the penis. Solubilizers, complexing agents and other additives may also be present in the composition.

Because the composition is topical and therefore non-invasive, it has particular advantages over the prior art, such as localized effect, targeted delivery, minimal if any systemic side effects, and achievement of substantially normal physiological erection. No hospitalization is required resulting in savings of both pain and expense. Because no internal or external physical devices are used, a greater sense of the erection being natural is obtained. This results in a psychological benefit to the sexual partners. There is no discomfort due to the composition during coitus. In fact, the topical vehicle of the composition may act as a lubricant and aid in coitus. These are significant advantages over the prior art.

Numerous other advantages and features of the present invention will become readily apparent from the following detailed description of the invention, the accompanying examples and the appended claims.

BRIEF DESCRIPTION OF THE DRAWINGS

FIG. 1 is a graph illustrating the effect of the weight percent of hydroxypropyl-β-cyclodextrin in the composition on the amount of papaverine released from the gel composition and the rate thereof.

DETAILED DESCRIPTION OF THE PREFERRED EMBODIMENTS

While this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

In this application, the term "non-invasive" means the treatment does not require puncturing of the skin, surgical removal of tissue, or any other kind of surgical intervention.

In this invention, a peripheral vasodilator which enhances the maintenance of penis erection by a male is combined with a pharmacologically acceptable enhancer to facilitate absorption of the vasodilator through the skin and a pharmacologically acceptable topical vehicle. Preferably the topical vehicle is a gel. The pharmacologically acceptable enhancer is a cyclodextrin, such as α-cyclodextrin, β-cyclodextrin, γ-cyclodextrin and 2-methylcyclodextrin. This most preferred cyclodextrin for the composition herein is hydroxypropyl-β-cyclodextrin (HPBCD herein). This invention is particularly useful to diabetic men who have become impotent as a result of their diabetes.

The peripheral vasodilators preferred for the present purposes are isoquinoline ethers represented by the following general formula:

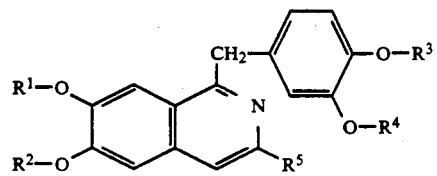

Wherein $R^1$, $R^2$, $R^3$ and $R^4$ are alike or different and are alkyl groups containing one to four carbon atoms, i.e., methyl, ethyl, n-propyl, isopropyl, n-butyl, sec-butyl and t-butyl, $R^5$ is hydrogen or methyl. Particularly preferred are the isoquinoline ethers papaverine, dioxylin and ethaverine. The isoquinoline ethers having peripheral vasodilating activity may be used in a free base form or as a pharmacologically acceptable acid addition salt.

Acid addition salts of the isoquinoline ethers suitable for the purposes of this invention can be prepared by neutralization of the free base with an appropriate amount of an inorganic or organic acid, examples of which are hydrochloric, hydrobromic, sulfuric, nitric, phosphoric, acetic, lactic, benzoic, salicylic, glycolic, succinic, tartaric, maleic, malic, pamoic, cyclohexanesulfamic, citric, methanesulfonic, and like acids. Pharmacologically acceptable salts of the preferred isoquinoline ethers include papaverine hydrochloride, dioxylin phosphate and ethaverine hydrochloride.

The neutralization can be carried out by a variety of procedures known in the art to be generally useful for the preparation of amine acid addition salts. The choice of the most suitable procedure will depend on a variety of factors including convenience of operation, economic considerations and, particularly, the solubility characteristics of the free base, the acid to be used, and the acid addition salt to be formed. If the acid is soluble in water, the free base can be dissolved in water containing an equivalent amount of the acid, and thereafter, the water can be removed by evaporation. In some instances, the salt precipitates from the aqueous solution, particularly when cooled, and evaporation is not necessary.

If the acid is soluble in a relatively non-polar solvent, such as dimethyl ether or diisopropyl ether, for example, separate solutions of the acid and free base in such a solvent can be mixed in equivalent amounts, whereupon the acid addition salt will usually precipitate because of its relatively lower solubility in the nonpolar solvent. Alternatively, the free base can be mixed with an equivalent amount of acid in the presence of a solvent of moderate polarity, for example, a lower alkanol, a lower alkanone, or a lower alkyl ester of a lower alkanoic acid. Examples of these solvents are ethanol, acetone, and ethyl acetate, respectively. Subsequent admixture of the resulting solution of acid addition salt with a lower polarity solvent such as dimethyl ether or hexane, for example, will usually cause precipitation of the acid addition salt.

The concentration of the peripheral vasodilator in the carrier, i.e. the topical vehicle, is about 1 to about 10 percent by weight, preferably about 3 to about 6 percent by weight.

An alpha receptor blocker may be combined with the peripheral vasodilator, if desired. A preferred alpha receptor blocker is phentolamine which is represented by the formula:

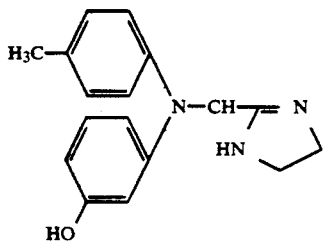

Other suitable alpha receptor blockers are phenoxybenzamine, yohimbine, prazosin, tolazoline and the like. These blockers are usually present in a concentration of about 0.05 to about 0.5 percent by weight of the composition. The weight ratio of peripheral vasodilator to alpha receptor blocker usually is in the range of about 20:1 to about 200:1, preferably about 30:1 to about 50:1. Optionally, the present compositions can also include androgens such as testosterone and the like.

Maintenance of penis erection may be further enhanced by restricting blood flow from the penis after the erection is enhanced by the peripheral vasodilator. One method of accomplishing reduced blood flow is to add a vasoconstrictor to the composition. The action of the vasoconstrictor should be time delayed to act upon the penis after the peripheral vasodilator has enhanced the maintenance of the penis erection This time delay may be accomplished by utilizing water-insoluble, lipophilic norepinephrine salts (such as benzoate) which will slowly be absorbed through the skin of the penis. Suitable vasoconstrictors are epinephrine, norepinephrine, phenylepinephrine, and the like. The weight ratio of vasodilator to vasoconstrictor in the present compositions is usually in the range of about 10,000:1 to about 1,000:1, preferably about 6,000:1 to about 2,000:1. Alternatively, blood flow from the penis may be restricted by the use of known mechanical devices.

The vasoconstrictor may also minimize delivery of the peripheral vasodilator and alpha receptor blocker to the systemic circulation. Thereby prolonging the action of the peripheral vasodilator locally and reducing systemic reactions.

The topical vehicle is water-soluble, non-irritating, and does not sensitize the skin. In a preferred embodiment of the composition the topical vehicle has a semi-soft, cream-like consistency. This can be obtained by the use of a hydrogel such as hydroxypropylmethylcellulose. A suitable methylcellulose is Methocell E4M which is available from Dow Chemical, Inc. Alternatively, an acrylic acid polymer can be used to obtain a topical vehicle of the desired consistency. Carbopol 934P, commercially available from B. F. Goodrich Co., when neutralized, is a suitable acrylic acid polymer for this purpose. The weight percent of the polymer in the composition is in the range of about 0.1 to about 5.

Improved results are obtained by the use of HPBCD in the composition. HPBCD is a cyclic polymer having a doughnut-shaped molecular structure including an inner cavity. While the mechanism is not clear, it is understood that an inclusion compound is formed with the HPBCD. This makes the composition more readily absorbed by the skin. While HPBCD is the more preferred cyclodextrin constituent, other cyclodextrins can also be used. The weight percent of the HPBCD in the composition preferably is in the range of about 1 to about 10.

HPBCD is a commercially available compound that is derived from beta-cyclodextrin by condensation with a propylene oxide to provide the corresponding hydroxypropyl derivative having a degree of substitution (D.S.) up to about 15 or higher. For the purposes of the present invention a D.S. value of about 5 to about 7 is preferred.

The preparation of a suitable HPBCD is described, inter alia, in International Journal of Pharmaceutics 29 (1986):73–82 and in Journal of pharmaceutical Sciences 75(6):571–572 (1986). Also known, and contemplated for the purposes of the present invention is the HPBCD that is a polyether of a cyclodextrin and is obtained by condensation of an excess of hydroxypropylene oxide with beta-cyclodextrin as described in U.S. Pat. No. 3,459,731 to Gzamera et al.

It is important that the pH of the composition be in the range of about 7 to about 8, preferably 7.4, to maximize the availability of the free base form of the vasodilator and thus to maximize skin absorption. Ammonium hydroxide or sodium hydroxide can be used to adjust the pH.

The remaining components of the composition are water and monohydric and polyhydric alcohols such as ethanol, polyethylene glycol and propylene glycol. The weight percent of water in the composition is in the range of about 20 to about 60 and that of the alcohols about 80 to about 40. Ethanol and propylene glycol preferably are present in a relative weight ratio of about 3:1 to about 0:1.

The following Table I describes typical formulations of the invention, but are not to be construed as a limitation thereon.

TABLE I

REPRESENTATIVE TOPICAL PAPAVERINE GELS

| Ingredients, wt % | Gel Preparation | | | | | | |
|---|---|---|---|---|---|---|---|
| | A | B | C | D | E | F | G |
| Papaverine HCl[1] | 3.0 | 3.0 | 3.0 | 3.0 | 3.0 | 3.0 | 3.0 |
| Phentolamine myselate[2] | 0.1 | 0.1 | 0.1 | 0.1 | 0.1 | 0.1 | 0.1 |
| Norepinephrine[3] | 0.001 | 0.001 | 0.001 | 0.001 | 0.001 | 0.001 | 0 |
| Ethanol | 35.0 | 30.0 | 30.0 | 35.0 | 35.0 | 35.0 | 35.0 |
| Propylene | 15.0 | 20.0 | 20.0 | 15.0 | 15.0 | 15.0 | 15.0 |
| Hydroxypropyl-methylcellulose[4] | 2.0 | 2.0 | 1.5 | 0 | 0 | 0 | 0 |
| Acrylic Acid Polymer[5] | 0 | 0 | 0 | 1.0 | 1.0 | 1.0 | 1.0 |

TABLE I-continued

REPRESENTATIVE TOPICAL PAPAVERINE GELS

| Ingredients, wt % | Gel Preparation | | | | | | |
|---|---|---|---|---|---|---|---|
| | A | B | C | D | E | F | G |
| Hydroxypropyl-β-cyclodextrin | 1.0 | 0 | 1.5 | 1.0 | 0 | 1.0 | 1.0 |
| NH₄OH, q.s. (pH) | 7-8 | 7-8 | 7-8 | 7-8 | 7-8 | 7-8 | 7-8 |
| Menthol[6] | 0 | 1.0 | 0 | 0 | 1.0 | 0 | 0 |
| Water | 43.899 | 43.899 | 43.899 | 44.899 | 44.899 | 44.899 | 44.9 |
| Total | 100 | 100 | 100 | 100 | 100 | 100 | 100 |

[1] A peripheral vasodilator which can be substituted by other peripheral vasodilators.
[2] An alpha receptor blocker which can be substituted by other alpha receptor blockers.
[3] A vasoconstrictor which can be substituted by other vasoconstrictors.
[4] Methocell E4M from Dow Chemical Co., Inc.
[5] Carbopol 934P from B. F. Goodrich Co.
[6] Added to further enhance absorption through the skin.

EXAMPLE 1

Methods for Making the Topical Gel Compositions

The above compositions in Table I can be manufactured according to the following procedures:

Procedure A

Preparation of the topical vehicle:
  weigh the desired amount of hydroxypropylmethylcellulose;
  disperse the hydroxypropylmethylcellulose in about one half of the total amount of ethanol;
  heat the obtained dispersion to a temperature of about 50° to about 60° C., for about 10-20 minutes;
  in a separate vessel, mix the remaining amount of ethanol and all of the propylene glycol, and thereafter cool the mixture to about 5° to 10° C. and maintain the cooled mixture at that temperature for about 30 to 60 minutes;
  combine the foregoing two admixtures to form a homogeneous, viscous composition.

Preparation of a solution of active ingredients:
  weigh the desired amounts of the peripheral vasodilator and the optional vasoconstrictor and/or the alpha receptor blocker;
  dissolve the peripheral vasodilator and the optional vasoconstrictor and/or alpha receptor blocker in the total amount of water required;
  weigh the desired amount of HPBCD and dissolve it in the water solution of the peripheral vasodilator and the aforementioned optional active ingredients; and
  adjust the pH of the solution to a value of about 7 to 8 with ammonium hydroxide.

The solution of the active ingredients is then combined with the prepared topical vehicle to form the composition.

Procedure B

Preparation of the topical vehicle:
  weigh the desired amount of the acrylic acid polymer;
  disperse the acrylic acid polymer in about one-half of the total amount of water;
  adjust the pH of the resulting dispersion to a value of about 7 to 8 with ammonium hydroxide; and
  maintain the resulting composition at about ambient temperature for about 18 hours to obtain the desired viscous consistency.

Preparation of a solution of active ingredients:
  weigh the desired amounts of the peripheral vasodilator and the optional vasoconstrictor and/or alpha receptor blocker;
  dissolve the peripheral vasodilator and the optional vasoconstrictor and/or alpha receptor blocker in the total amount of ethanol and propylene glycol;
  weigh the desired amount of HPBCD and dissolve it in the remaining amount of water;
  combine the obtained aqueous HPBCD solution with the alcoholic solution of the peripheral vasodilator and the aforementioned optional active ingredients; and
  adjust the pH of the combined solutions with ammonium hydroxide to a value of about 7 to about 8.

Thereafter, the foregoing combined solutions containing the active ingredients are further combined with the prepared topical vehicle to form the composition.

The preferred topical papaverine gel compositions disclosed herein contain HPBCD. In the gel compositions, the weight percent of HPBCD exceeds the weight percent of papaverine. Table II hereinbelow enumerates several compositions, some that contain HPBCD and some that do not. Those that contain HPBCD are examples of the preferred compositions. Those compositions that do not contain HPBCD are used to illustrate the advantages of HPBCD-containing compositions in the following examples.

TABLE II

REPRESENTATIVE TOPICAL PAPAVERINE GELS

| Ingredients (wt. %) | Gel Preparation | | | | | |
|---|---|---|---|---|---|---|
| | 1 | 2 | 3 | 4 | 5 | 6 |
| Papaverine | 0.5 | 1 | 1 | 2 | 1 | 1 |
| HPBCD | 1.5 | — | 3 | — | 3 | 3 |
| Ethyl Alcohol | 20 | 10 | 20 | 10 | 20 | 45 |
| Methocel E4M | 2 | 2 | 2 | 2 | 2 | 3 |
| Water | 76 | 77 | 74 | 76 | 64 | 48 |
| Propylene Glycol | — | 10 | — | 10 | 10 | — |
| Total | 100 | 100 | 100 | 100 | 100 | 100 |

EXAMPLE 2

Method for Making Preferred Gel Composition Containing HPBCD

The topical papaverine gels in Table II above were made according to the following detailed procedure. For clarity, preparation of a particular gel, number six in Table II hereinabove, is illustrated. It would be apparent to one skilled in the art that all of the topical papaverine gels in Table II can be prepared according to the procedure in this example.

Distilled water (164 grams) was added to a beaker and heated to approximately 50° to 60° C. while the water was stirred. Methocel (16.5 grams) was slowly dispersed into the heated water in about 15 minutes. Water (100 grams) was added to the solution while mixing. The solution was then cooled in an ice bath. The solution was chilled to about 10° to about 15° C. while being mixed for approximately 15 minutes. Hydroxypropyl-$\beta$-cyclodextrin (HPBCD)(16.5 grams) was mixed with ethyl alcohol (70 grams). The mixture was stirred for about 10 to 15 minutes until the HPBCD was completely dissolved.

A papaverine solution was prepared by adding papaverine (5.5 grams) to ethyl alcohol (177.5 grams). The mixture was stirred and heated to about 50° to about 60° C. for about 30 minutes until the papaverine was completely dissolved. The HPBCD and papaverine solutions were combined and stirred for about 5 minutes. The combined solution was then mixed with the methocel solution discussed hereinabove with a high torque stirrer for at least 15 to 20 minutes. The resulting mixture was packaged in small tubes (5 grams per tube).

EXAMPLE 3

Improved Flux of Topical Papaverine Gel Containing HPBCD Into Skin

A neat solution of papaverine containing one milligram of papaverine in 20 milliliters of ethanol was prepared. The neat solution and topical papaverine gel compositions 2 and 6 from Table II were then tested for their rate of flux through human stratum corneum epiderm skin samples. Gel 2 did not contain HPBCD, while gel 6 contained 3 percent by weight HPBCD. The flux of papaverine in these compositions through human skin samples was measured using Franz diffusion cells filled with degassed saline.

The amount of saline in the cells was first recorded. The dried skin samples were hydrated for one hour and then mounted on the Franz cells at a temperature of about 35° C. The surface temperature of the skin was about 32° C.

Aliquots of the neat solution and the topical papaverine gels were drawn into 1 ml syringes. Each filled syringe was weighed and a small amount of the gel or solution therein was placed on a skin sample and gently spread on its surface. The syringes were again weighed to determine the amount of gel applied. The skin surface was then isolated from the atmosphere.

Liquid samples were removed from the Franz cells over a 48 hour period. The samples drawn during the first two hours were not analyzed. The samples were replaced by an equal volume of saline. The concentration of papaverine in each sample was determined by a high performance liquid chromatography (HPLC) technique. The concentration of papaverine in the samples drawn from the Franz cells was determined by high pressure liquid chromatography. From this data, the rate of papaverine flux through the skin was calculated.

Table III illustrates the rate of flux of the neat papaverine and papaverine gel compositions with and without HPBCD therein through the skin. The results indicate that the topical papaverine gel with HPBCD, composition 6 from Table II, had superior flux over non HPBCD-containing papaverine gels, compositions 2 and 4 from Table II, or neat papaverine.

TABLE III

DIFFUSION OF PAPAVERINE THROUGH HUMAN SKIN SAMPLES

| Composition | Flux ($\mu$g/cm$^2$/hr) | Avg. Flux ($\mu$g/cm$^2$/hr) |
|---|---|---|
| Neat[1] | 0.0985 | |
| Neat[2] | 0.0992 | |
| | | 0.0988 |
| 2[1] | 0.164 | |
| 2[2] | 0.284 | |
| 2[3] | 0.340 | |
| | | 0.263 ± .09 |
| 4[3] | 0.772 | |
| 4[4] | 0.223 | |
| 4[5] | 0.397 | |
| | | 0.459 ± 0.249 |
| 6[4] | 0.474 | |
| 6[5] | 0.671 | |
| 6[4] | 0.626 | |
| | | 0.59 ± 0.08 |

[1] Skin sample from the abdomen of a 63 year old Hispanic female cadaver.
[2] Skin sample from the breast of a 33 year old Hispanic female by gynacomastic surgery.
[3] Skin sample from the breast of an 18 year old Black female by elective surgery.
[4] Skin sample from the stomach of an 89 year old white male.
[5] Skin sample from the stomach area of a 64 year old white female.

EXAMPLE 4

Flux of Topical Papaverine Gels Through Whole Glans Penis Skin

The flux of a topical papaverine gel formula containing HPBCD (composition 6 from Table II) was compared with the flux of a topical papaverine gel formula that did not contain HPBCD (composition 2 from Table II) and a neat papaverine preparation. The topical papaverine gel and neat papaverine were applied onto the glans penis skin samples mounted on Franz cells as described in Example 3. The results of this comparison are summarized in Table IV below. The flux of papaverine from the HPBCD-containing papaverine gel composition was greater than the flux of the papaverine from the composition that did not contain HPBCD.

TABLE IV

TOPICAL PAPAVERINE GEL PERMEATION THROUGH DIFFERENT TYPES OF WHOLE GLANS PENIS SKIN

| Composition | Skin Type | Amount Applied (mg) | Flux $\mu$g/cm$^2$/hr | Avg. Flux $\mu$g/cm$^2$/hr |
|---|---|---|---|---|
| Neat | A | 1.0 | 0.02 | |
| Neat | B | 1.0 | 3.10 | |
| Neat | G | 1.0 | 0.47 | |
| Neat | H | 1.0 | 0.28 | |
| | | | | 0.97 ± 1.43 |
| 2 | C | 2.346 | 0.845 | |
| 2 | D | 1.524 | 1.390 | |
| 2 | E | 1.755 | 1.96 | |
| 2 | F | 2.294 | 4.11 | |
| | | | | 2.08 ± 1.43 |
| 6 | C | 1.103 | 0.861 | |
| 6 | D | 1.246 | 1.470 | |
| 6 | F | 2.421 | 4.470 | |
| | | | | 2.27 ± 1.93 |

A. 30 year old white male
B. 61 year old white male
C. 35 year old white male
D. 38 year old white male
E. 81 year old white male
F. 60 year old white male
G. 45 year old white male
H. 70 year old white male

EXAMPLE 5

Effect of Papaverine:HPBCD Mole Ratio on Papaverine in vitro Rate of Release from Composition The rate of in vitro release of papaverine from compositions with varying concentrations of HPBCD therein was measured through a dialysis membrane to determine the optimum molar ratio of papaverine to HPBCD in the composition. Referring to TABLE V, 1% by weight papaverine in gel compositions with different concentrations of HPBCD (2, 4, 8 and 10 wt %) were prepared according to the procedure detailed above. Non-HPBCD containing compositions were also prepared. Each composition was subjected to dialysis. Each reported in Tables V and VI below.

A spectrophotometric method at 235 nm using an Hitachi U-2000 Spectrophotometer was utilized to evaluate the samples. For this purpose a Beer's law plot was prepared on ethanol solutions of papaverine.

An aqueous phosphate buffer solution with ethyl alcohol in a volume ratio of 60 to 40, respectively, was added to a 250 ml capacity beaker to a depth of 2-3 cm. A cellophane molecular porous membrane with a molecular weight cutoff range of 6,000 to 8,000 with a papaverine composition thereon was applied to the open end of a glass tube. The glass tube was 2.5 cm in diameter and 10 cm in length. The cellophane membrane was secured to the open end of the glass tube with a rubber band. The tube was placed in the center hole of a beaker cover. The hole had a diameter greater than that of the test tube, so tape was placed on the closed end of the test tube so that closed would fit snugly in the hole. The beaker cover with the glass tube therein was then placed onto the beaker. The glass tube was adjusted in the cover so that about 1 cm of the end with the cellophane membrane was submerged into the dialysis medium.

The papaverine composition was applied to the cellophane membrane by first cutting a piece of cellophane from the roll. The cut section was soaked in distilled water for about 24 hours and dried at room temperature for about one hour prior to use. An aliquot of the papaverine composition was accurately weighed and applied to the center portion of the cellophane cut section that corresponds to the diameter of the glass tube. The cellophane membrane was fixed to the glass tube so that the papaverine composition was on the inside of the test tube. The tube was assembled with the beaker as described above.

The papaverine composition was dialyzed by first submerging the cellophane-covered end of the tube in the dialysis medium and immediately placing the beaker with the tube partially submerged therein (the dialysis cell) in a hot air oven preheated to 37° C. Samples of the dialysis medium (5 ml) were withdrawn at 10, 20 and 30 minute-time intervals. The withdrawn volume was replaced in each instance with 5 ml of fresh dialysis medium.

The gel compositions contained 1 gram of gel which was 60% by weight water, 38% by weight ethanol and 2% by weight methanol. The molecular weight of HPBCD (MW approx. 1163) is about four times that of papaverine (MW approx. 327). From Table V it is apparent that the composition with a mole ratio of papaverine to HPBCD of about 1:1 (4% HPBCD) exhibited vastly superior release and rate of release of papaverine than compositions with higher or lower papaverine to HPBCD mole ratios.

TABLE V

IN VITRO RELEASE OF PAPAVERINE FROM GEL COMPOSITION

| Composition | Amount of Papaverine (mg) | Amount of Papaverine (mg) Released From 1 Gram of Gel | Rate of Release $mg/cm^2/min$ | Variance $r^2$ |
|---|---|---|---|---|
| 1 wt. % papaverine in gel base containing: | | | | |
| 0% HPBCD | 10 | 0.66 | 0.162 | 0.9779 |
| 2% HPBCD | 10 | 0.48 | 0.184 | 0.9742 |
| 4% HPBCD | 10 | 1.31 | 0.603 | 0.9894 |
| 6% HPBCD | 10 | 0.46 | 0.098 | 0.9529 |
| 8% HPBCD | 10 | 0.48 | 0.160 | 0.9927 |
| 10% HPBCD | 10 | 0.33 | 0.139 | 0.9835 |
| 2 wt % papaverine in gel base containing: | | | | |
| 6% HPBCD | 20 | 0.775 | 0.203 | |

Referring to FIG. 1, the release rate of papaverine and the amount of papaverine released from the 1% by weight papaverine topical gel composition was plotted as a function of the weight percent of HPBCD in the composition. FIG. 1 illustrates superior performance of a 1% by weight papaverine gel composition when the HPBCD is present in an amount of about 3 to about 5 weight percent. This corresponds to a mole ratio range of papaverine to HPBCD of about 1:0.8 to about 1:1.4. The preferred papaverine:HPBCD mole ratio is about 1:1 (4 weight percent HPBCD and 1 weight percent papaverine) in the composition.

Obviously, for the papaverine to be effective, it must be released from the gel composition. Table VI illustrates the release and rate of release of papaverine from gels containing buffers and surfactants and solutions of papaverine. TABLE VI illustrates that, even when the amount of papaverine in non-HPBCD containing compositions tested using the above detailed dialysis procedure was three times the amount of papaverine in the HPBCD-containing compositions, the papaverine release and rate of release were greater in the HPBCD-containing compositions with an optimum molecular weight ratio of papaverine:HPBCD. This result is totally unexpected, as solutions of papaverine would be expected to release the papaverine more readily than gel compositions containing papaverine.

TABLE VI

| Composition | Amount of Papaverine (mg) | Amount of Papaverine Released from 1 Gram of Gel (mg) | Papaverine Rate of Release $(mg/cm^2/min)$ | Variance $r^2$ |
|---|---|---|---|---|
| 3 wt % Papaverine in Gel Base Containing: | | | | |
| buffer[1] + 5% Tween 80[2] | 30 | 0.70 | 0.268 | 0.9951 |
| buffer + 10% Tween 80[2] | 30 | 0.81 | 0.37 | 0.9950 |
| aqueous solution of 5% Tween 80 | 30 | 0.59 | 0.173 | 0.9906 |
| buffer + 5% Emulphor EL-719L[3] | 30 | 0.48 | 0.183 | 0.9707 |
| aqueous solution of 5% Emulphor EL-719L | 30 | 0.84 | 0.26 | 0.9379 |

TABLE VI-continued

| Composition | Amount of Papaverine (mg) | Amount of Papaverine Released from 1 Gram of Gel (mg) | Papaverine Rate of Release (mg/cm²/min) | Variance r² |
|---|---|---|---|---|
| 3 wt % Papaverine Solution: | | | | |
| ethanol + 10% Tween 80 | 30 | 0.886 | 0.304 | 0.9109 |
| ethanol + 5% Tween 80 | 30 | 1.46 | 0.54 | 0.9951 |
| ethanol + 5% Emulphor El-719L | 30 | 1.25 | 0.295 | 0.9696 |
| ethanol | 30 | 1.2 | 0.45 | 0.9921 |

[1] pH 7.4 phosphate buffer.
[2] polyoxyethylene (20) sorbitan, a non-ionic mono-oleate with an HLB of 15.
[3] polyoxylated vegetable oil, PEG (40), castor oil.

EXAMPLE 6

Method of Applying Topical Gel to a Patient

To enhance an erection, a sufficient amount of the present composition is applied directly to the penis prior to coitus. The topical composition containing papaverine and HPBCD is applied liberally to the penis shaft, glans, scrotum and perineum. The composition is massaged into the skin for about one minute. Preferably, the application is made about 30 minutes to about 1 hour prior to coitus; however, the time of application may vary from patient to patient.

An effective amount or dosage needed to enhance an erection usually is about 50 to about 500 milligrams of the peripheral vasodilator per application. Preferably, about 75 to about 150 milligrams of the peripheral vasodilator are applied to the penis each time.

EXAMPLE 7

Trials in Patients

A number of trials have been conducted under physician supervision in volunteers diagnosed with premature ejaculation and who have not been able to maintain an erection for coitus. These patients were young, healthy subjects with normal vascular integrity and were undergoing treatment with intracavernosal injections of 30 mg doses of papaverine as part of a therapeutic regimen. These injections were substituted with a topical hydrogel formulation (Preparation 6 in Table II; 50 mg dose of papaverine). The patients were asked for a subjective evaluation of efficacy based on the quality of their erection (rigidity) and the duration of action. The patients were instructed to apply the topical preparation in the following manner;

1. Empty entire contents (5 grams) of one tube into palm of hand.
2. Apply gel liberally to penis shaft, glans, scrotum and perineum; massage thoroughly into the skin for one minute.
3. Apply a condom to prevent transmisson of the drug to the patient's partner.

Of nineteen subjects who participated, 4 reported no effect, 5 reported rigidity equivalent to the injection treatment, and the remainder reported moderate degrees of tumescence and duration. There were no reports of irritation. In those patients that experienced a positive response to treatment, the duration of their erections were approximately 10-15 minutes as compared to one hour with injection, and 2 minutes or less with no drug treatments.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

I claim:

1. An aqueous topical composition suitable for enhancing the maintenance of penis erection by a male patient which comprises a peripheral vasodilator and hydroxypropyl-$\beta$-cyclodextrin present in a molar ratio in the range of about 1 to 0.8 to about 1 to 1.4, respectively, and in a pharmacologically acceptable topical vehicle for said vasodilator; said peripheral vasodilator being present in an amount sufficient to enhance penis erection.

2. The composition in accordance with claim 1 wherein the peripheral vasodilator is an isoquinoline ether.

3. The composition in accordance with claim 1 wherein the peripheral vasodilator is a member of the group consisting of papaverine, dioxyline and ethaverine.

4. The composition in accordance with claim 1 wherein the peripheral vasodilator is present in an amount in the range of about 1 to about 10 percent by weight of the composition.

5. The composition in accordance with claim 1 wherein the hydroxypropyl-$\beta$-cyclodextrin is present in an amount in the range of about 1 to about 10 percent by weight of the composition.

6. The composition in accordance with claim 1 wherein the peripheral vasodilator is papaverine and the molar ratio of papaverine to hydroxypropyl-$\beta$-cyclodextrin is about 1:1.

7. The composition in accordance with claim 1 wherein the peripheral vasodilator is represented by the following general formula:

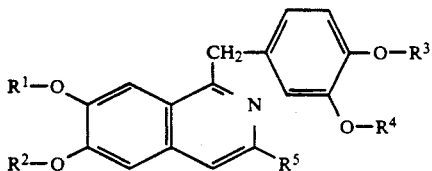

wherein $R^1$, $R^2$, $R^3$ and $R^4$ are alike or different and are alkyl groups containing one to four carbon atoms, i.e., methyl, ethyl, n-propyl, isopropyl, n-butyl, sec-butyl and t-butyl, and $R^5$ is hydrogen or methyl and is present in a concentration of about 1 to about 10 percent by weight of the vehicle.

8. The composition in accordance with claim 1 further including an alpha receptor blocker.

9. The composition in accordance with claim 8 wherein said alpha receptor blocker is phentolamine.

10. The composition in accordance with claim 1 wherein said topical vehicle consists of a combination of an alcohol and a glycol.

11. The composition in accordance with claim 1 wherein the topical vehicle is a hydrogel having a semi-soft, cream-like consistency.

12. The composition in accordance with claim 11 wherein said hydrogel is hydroxypropylmethylcellulose.

13. The composition in accordance with claim 1 wherein the pH is about 7.4.

14. The composition in accordance with claim 1 further including a vasoconstrictor.

15. The composition in accordance with claim 14 wherein the vasoconstrictor is a member of the group consisting of epinephrine and phenylephrine.

16. A method for enhancing the maintenance of penis erection by a male patient which comprises the topical application to the penis of an effective, erection enhancing, amount of a composition comprising a peripheral vasodilator and a hydroxypropyl-$\beta$-cyclodextrin in a pharmacologically acceptable topical vehicle for said vasodilator and said hydroxypropyl-$\beta$-cyclodextrin; said composition having a pH value of about 7 to about 8 containing about 1 to about 10 percent by weight of said hydroxypropyl-$\beta$-cyclodextrin; and the concentration of said vasodilator being in the range of about 1 to about 10 percent by weight of said vehicle.

17. The method in accordance with claim 16 wherein the peripheral vasodilator is papaverine.

18. The method in accordance with claim 16 wherein the peripheral vasodilator is papaverine and wherein the composition additionally includes phentolamine.

19. The method in accordance with claim 16 further comprising a means for restricting blood flow from the penis after the penis erection is enhanced.

20. The method in accordance with claim 19 wherein the means for restricting blood flow from the penis is a vasoconstrictor.

21. The method in accordance with claim 19 wherein the vasoconstrictor is a member of the group consisting of epinephrine and phenylephrine.

* * * * *

UNITED STATES PATENT AND TRADEMARK OFFICE
CERTIFICATE OF CORRECTION

PATENT NO. : 5,256,652
DATED : October 26, 1993
INVENTOR(S) : Ragab El-Rashidy

It is certified that error appears in the above-identified patent and that said Letters Patent is hereby corrected as shown below:

Col. 5, in the formula, "CH" should be -- $CH_2$ --.

Col. 5, line 37, after "erection" insert a period (.).

Col 11, line 15, after "Each" insert -- experiment was done in triplicate and the mean value --.

Signed and Sealed this

Fourteenth Day of June, 1994

Attest:

BRUCE LEHMAN

*Attesting Officer*     *Commissioner of Patents and Trademarks*